United States Patent
Werzinger et al.

(10) Patent No.: US 6,859,270 B2
(45) Date of Patent: Feb. 22, 2005

(54) METHOD AND DEVICE FOR INSPECTING TRANSPARENT CONTAINERS

(75) Inventors: Lothar Werzinger, Regensburg (DE); Stefan Piana, Köfering (DE)

(73) Assignee: Krones AG, Neutraubling (DE)

( * ) Notice: Subject to any disclaimer, the term of this patent is extended or adjusted under 35 U.S.C. 154(b) by 105 days.

(21) Appl. No.: 09/914,536

(22) PCT Filed: Mar. 21, 2001

(86) PCT No.: PCT/EP01/03237
§ 371 (c)(1),
(2), (4) Date: Jan. 28, 2002

(87) PCT Pub. No.: WO01/92860
PCT Pub. Date: Dec. 6, 2001

(65) Prior Publication Data
US 2003/0035103 A1 Feb. 20, 2003

(30) Foreign Application Priority Data
May 31, 2000 (DE) .......................... 100 27 226

(51) Int. Cl.⁷ ............................................. G01N 21/00
(52) U.S. Cl. ................................ 356/239.1; 356/240.1; 250/223
(58) Field of Search .................... 356/239.1, 240.1, 356/240; 250/223

(56) References Cited

U.S. PATENT DOCUMENTS

| | | | | |
|---|---|---|---|---|
| 5,095,204 A | * | 3/1992 | Novini | .................. 250/223 B |
| 5,729,340 A | * | 3/1998 | Griesbeck et al. | ....... 356/240.1 |
| 5,917,602 A | * | 6/1999 | Bonewitz et al. | ........... 356/614 |
| 6,031,221 A | * | 2/2000 | Furnas | .................... 250/223 B |
| 6,067,155 A | * | 5/2000 | Ringlien | .................. 356/240.1 |
| 6,072,575 A | * | 6/2000 | Loll | ........................ 356/239.4 |
| 6,452,156 B2 | * | 9/2002 | Lindner | .................. 250/223 B |

FOREIGN PATENT DOCUMENTS

| | | |
|---|---|---|
| DE | 19904732 A | 9/1999 |
| FR | 2 726651 A | 5/1996 |
| FR | 2 742865 A | 6/1997 |
| WO | WO 95/04267 | 7/1994 |

\* cited by examiner

*Primary Examiner*—David Gray
*Assistant Examiner*—Magda Cruz
(74) *Attorney, Agent, or Firm*—Marshall, Gerstein & Borun LLP

(57) ABSTRACT

A process for inspecting transparent containers (B), in which every container is illuminated and at least two exposures of the same container are produced by means of a single CCD camera (K) and evaluated, whereby one exposure images the container profile and the other exposure images the container wall, the exposure time of the CCD camera (K) is changed, between the two exposures, from an exposure time for a container to an exposure time for a container profile. A control device (C2) for changing the sensitivity of exposure of the CCD camera (K) is produced.

9 Claims, 1 Drawing Sheet

METHOD AND DEVICE FOR INSPECTING TRANSPARENT CONTAINERS

REFERENCE TO RELATED APPLICATIONS

This disclosure claims the benefit of the filing date of International Application No. PCT/EP01/03237, having an international filing date of Mar. 21, 2001, which designated the United States of America, and this disclosure is the United States national stage of that international application. This disclosure further claims priority to Germany patent application 100 27 226.6, filed May 31, 2000.

FIELD OF THE INVENTION

The invention relates to a process and a device for inspecting transparent containers in beverage bottling operations.

BACKGROUND OF THE INVENTION

In the inspection of transparent containers, particularly beverage bottles, two camera systems and at least two illumination systems, if applicable, are, as a general rule, used in order to carry out the evaluation of the container wall (inspecting of the side wall) and the evaluation of the container contour, because an illumination other than the one used for the evaluation of the wall is necessary for the evaluation of the contour. The inspection device is thus made more expensive by the two camera systems. In addition, the expense for maintenance is high (DE 19 904 732 A).

In the German patent document DE 19 904 732 A, it is proposed to use a single CCD camera for the two exposures, to use a maximum intensity of illumination for the exposure of the wall of the container, and to reduce the intensity of illumination for the exposure of the contour of the same container.

SUMMARY OF THE INVENTION

The task which forms the basis of the invention is that of devising a process of the type stated above, as well as a device that is suitable for carrying out the process, by means of which a reliable evaluation of the wall and evaluation of the contour are possible in another way by means of one single CCD camera.

Both the optimally exposed image of the wall, as well as the optimally exposed image of the contour, can be produced by changing the sensitivity of exposure of the single CCD camera. The sensitivity of exposure is, as a variable process parameter, important precisely in regard to the presuppositions which are decisive for the quality of both of the exposures precisely at the point where the images ultimately arise—that is to say, in the CCD camera. In this way, optimally exposed images of the contour and of the wall are formed, from which a high reliability of evaluation results. It is obvious that the container that is inspected during the inspection can, if necessary, be rotated in order to obtain, with several first and second exposures, a comprehensively complete image of the wall of the container or of the course of contour of the container. A container can, however, also be depicted over its full circumference by means of only a single first and second exposure if optical devices, such as mirror apparatuses or the like, are used, which devices simultaneously produce several images of the container, exposed in a circumferentially-shifted manner, in only a single camera image. Suitable apparatuses, such as in WO 95/0427, for example, are already known.

The device manages to work with a single CCD camera, the sensitivity of exposure of which is modified in such a manner that the image of the wall and the image of the contour are exposed in an optimal manner. Even the smallest damages to or contaminations of the wall, or deviations in the contour, can also be determined with only a minimal expense for equipment. In addition, the device is maintenance-friendly, because few components that require maintenance are present.

The specific first and second exposure are formed, in a manner that is simple in terms of technical process, at the same intensity of illumination. The illumination can take place, in a preferred manner, by means of flashes, such as by means of an LED luminous screen, for example. An expensive, controllable illumination device, with zones of brightness which can be adjusted in different manners, is not necessary.

The exposures of a container taking place in a time-staggered manner are stored in memory, whereby the evaluation (contour, wall) can be carried out later, in either a temporally parallel or a sequential manner.

In accordance with the device, a control device is used, which device changes the sensitivity of exposure of the CCD camera by changing the exposure time in an optimized or in an alternating manner, as the case might be. This can be brought about, in several trigger positions, by means of an electronic control circuit.

The source of illumination is, in a suitable manner, at least one LED radiant field which can, in a preferable manner, be activated in individual flashes. In this manner, the images can be produced with great sharpness and at a uniform exposure.

The source of illumination of the CCD camera can either be positioned on opposite sides of the path of movement of the container (examination of transmitted light), or else on the same side (examination of incident light).

BRIEF DESCRIPTION OF THE DRAWINGS

One form of implementation of the object of the invention is illustrated by means of the diagrams. These depict the following.

DETAILED DESCRIPTION OF THE INVENTION

In a device (V) for inspecting transparent containes (B), such as beverage bottles of glass or of plastic, for example, each container (B) in a series of containers being continuously moved forward is inspected, during its passage through the device, in regard to the quality of its container wall (W), as well as the contour (P) of the same. Containers with contaiminations and/or damages and/or impermissible deviations in their contour should be detected and subsequently separated out. Each container (B) is transported through an inspection area on a conveying device (F). The conveying device (F) has two conveyor belts (1, 2), for example, which are driven in the same direction but at different speeds, in order to simultaneously rotate the container (B) around its vertical axis during the transport movement. A source of illumination (L), such as at least one LED radiant field (3), for example, which source can be activated to individual flashes by means of an electronic control device (C1), is positioned on one side of the conveying device (F). For example, a single CCD camera (K) is positioned on the opposite side and oriented towards the inspection area in which the exposure of the container are formed and, in specific terms, two different exposures are made, namely, an exposure of the wall and an exposure of the contour, each in an alternating manner. An electronic control device (C2) is provided for the CCD camera.

Figure 1:
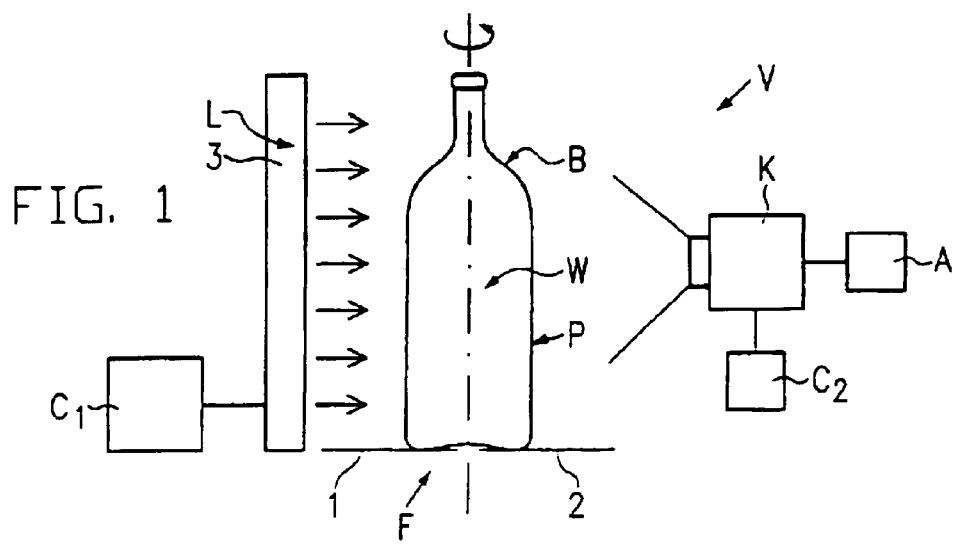
FIG. 1: In schematic terms, a cross-section through a device for inspecting transparent containers.
Figure 2:
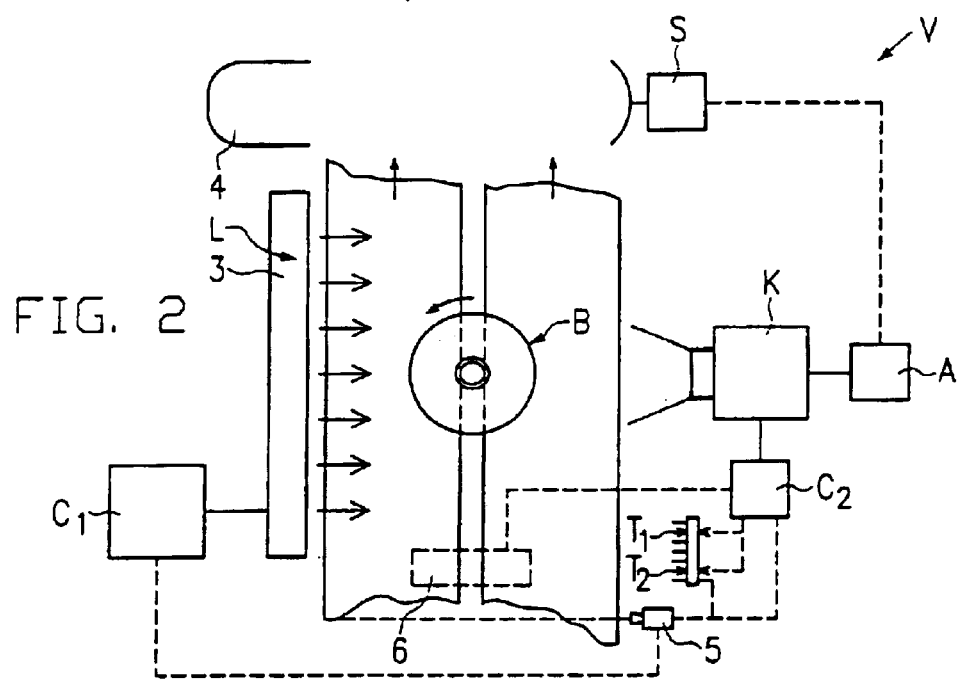
FIG. 2: A schematic view from above of FIG. 1.

An evaluation device (A) connected with the single CCD camera (K), in which device the images of the wall and the images of the contour are evaluated, can additionally be seen in the schematic view from above of FIG. 2. Upon the determination of a contamination and/or damage and/or a deviation in contour, a separating device (S) is activated, which device conveys the container (B) in question into a given area (4) (collecting bin, or the like).

A sensor (5), which can, for the clocking of the source of illumination (L) of the CCD camera (K), be connected with the control devices (C1, C2), is provided at the start of the inspection area. The control devices can additionally be connected with a rotational pacesetter of the drive unit (6) of the conveying device (F) in order to follow the container (B) in the inspection area in a manner dependent upon the conveying speed. This is suitable, for example, if several exposures of one container are to be carried out in different rotational positions. Trigger positions of a hardware type or of a software type (T1, T2) are taken into consideration during the inspection in order, for example, to change the sensitivity of exposure of the CCD camera (K), by means of the control device (C2), between the first and the sequentially-following second exposures in an alternating manner, in such a way that, in one exposure of the wall (first exposure), a different sensitivity of exposure is set than in another exposure of the contour (second exposure). In this, it is suitable to consider several trigger positions, such as in a multiple exposure of a container, for example.

Figure 3:
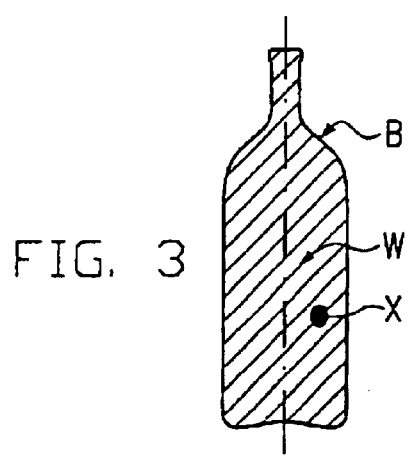
FIG. 3: In schematic form, an exposure of the wall.

In FIG. 3, an exposure of the wall of the container (B) is depicted schematically, in which, by adjusting the sensitivity of exposure—that is to say, the exposure time—of the CCD camera (K), an optimal exposure is provided for detecting contaminations and/or damages (X) either on or in the wall (W) of the transilluminated container, as the case may be. In actual practice, the image of the exposure of the wall is not optimal for the determination of the contour of the container. Normally, an illumination that is suitable for the exposure of the wall provides an image from which the outline of the container can only be detected with difficulty, which image is too bright for inspecting the contour.

Figure 4:
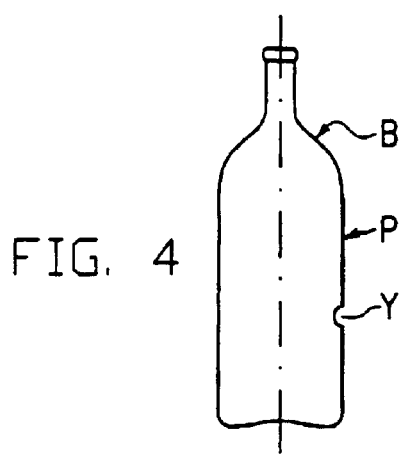
FIG. 4: In schematic form, an exposure of the contour of the container.

In the exposure of the contour in FIG. 4, on the other hand, the contour (P) of the container (B) is imaged in a sharp and meaningful manner, as represented by the solid outline, in order to detect deviations (Y) in the contour. In the exposure of the contour, the wall itself is not imaged in a manner which is sufficiently detailed in detection of flakes of dirt, etc. An exposure which is sufficient for inspecting the contour is, as a general rule, too dark for inspecting the wall.

If necessary, not only is the sensitivity of exposure of the CCD camera modified in such a manner that the exposures of the wall are exposed in an optimal manner for the exposure of the contour, but the intensity of illumination is also strongly modified for the equalization of different levels of transparency of the container through the fact, among other points, that the flash of the LED radiant field (3) is modified by means of the control device (C1), for example.

The sensitivity of the exposure or the exposure time for the container (B) which is optimal for the specific exposure of the wall or the exposure of the contour, respectively, is set in advance. During the inspection, the sensitivity of exposure is then adjusted back and forth between the values set in an alternating manner. By this means, it is thereby possible to scan the specific level of transparency of the container which is to be inspected, and to then set the specifically optimal trigger position (T1 or T2) or the sensitivity of exposure corresponding to this trigger position, as the case may be. In a similar manner, the flash time for the exposure of the wall or for the exposure of the contour, as the case may be, can be adjusted in an individual manner.

We claim:

1. A process for inspecting transparent containers (B), comprising the steps of illuminating every container (B) and producing by a single CCD camera at least two exposures of the same container, evaluating the exposures by an evaluation device, imaging a contour of the container with one exposure for the evaluation of the contour, imaging a wall of the container with another exposure for the evaluation of the wall, and changing over, between the two exposures, the exposure time of the CCD camera (K) from an exposure time for the container wall to an exposure time for the container contour.

2. A process in accordance with claim 1, further comprising the step of forming the two exposures in the same intensity of illumination.

3. A process in accordance with claim 2, wherein the step of forming the two exposures in the same illumination intensity is performed by means of flashes.

4. A process in accordance with claim 1, further comprising carrying out and storing in memory the two exposures of a container (B) one immediately after the other, and carrying out the evaluation of the exposures in one of in parallel or in succession, one after the other.

5. A device (V) for inspecting transparent containers (B), comprising in combination a container-conveying device (F), at least one source of illumination (L), a single CCD camera (K) which is connected with an evaluation device (A) for one or more exposures of the containers, one or more exposures of the container walls and one or more exposures of the container profiles being produced by means of said CCD camera (K), and a control device (C2) for changing the sensitivity of exposure of said CCD camera (K) between a sensitivity of exposure for the container profile and a sensitivity of exposure for the container walls.

6. A device in accordance with claim 5, wherein said control device (C2) has at least one electronic control circuit, by means of which the exposure time of said CCD camera (K) can be changed in at least two trigger positions (T1, T2).

7. A device in accordance with claim 5, wherein said source of illumination (L) comprises at least one LED radiant field (3) which can be activated in individual flashes.

8. A device in accordance with claim 7, further comprising a flash time adjusting device (C1) which is coordinated with said LED radiant field (3).

9. A device in accordance with claim 8, wherein said flash time adjusting device (C1) is an electronic control circuit which adjusts a flash time for a change of the intensity of illumination by means of different trigger positions.

* * * * *

UNITED STATES PATENT AND TRADEMARK OFFICE
CERTIFICATE OF CORRECTION

PATENT NO. : 6,859,270 B2
DATED : February 22, 2005
INVENTOR(S) : Lothar Werzinger et al.

It is certified that error appears in the above-identified patent and that said Letters Patent is hereby corrected as shown below:

<u>Title page,</u>
Item [57], ABSTRACT,
Line 10, change the last word from "produced" to -- provided --.

Signed and Sealed this

Sixteenth Day of August, 2005

JON W. DUDAS
*Director of the United States Patent and Trademark Office*